United States Patent [19]

Mochida et al.

[11] Patent Number: 4,482,636

[45] Date of Patent: Nov. 13, 1984

[54] METHOD FOR REACTING SOLID AND LIQUID PHASES

[75] Inventors: Ei Mochida; Takashi Kudo, both of Tokyo; Toshiyuki Sugawara, Saitama; Minoru Tsumura, Tokyo, all of Japan

[73] Assignee: Mochida Pharmaceutical Co., Ltd., Tokyo, Japan

[21] Appl. No.: 407,903

[22] Filed: Aug. 13, 1982

[30] Foreign Application Priority Data

Aug. 27, 1981 [JP] Japan .................................. 56-134534

[51] Int. Cl.$^3$ ...................... G01N 33/56; G01N 33/58; G01N 33/60; B01F 9/00
[52] U.S. Cl. ....................................... 436/518; 422/72; 435/7; 436/527; 436/531; 436/800; 436/804; 436/808; 436/813
[58] Field of Search ............... 436/518, 808, 813, 527, 436/531; 422/72; 435/7; 436/800, 804

[56] References Cited

U.S. PATENT DOCUMENTS

| 2,395,593 | 2/1946 | Trager ............................ 366/208 X |
| 3,790,663 | 2/1974 | Garrison et al. ...................... 422/62 |
| 4,090,848 | 5/1978 | Naono ..................................... 422/81 |
| 4,244,694 | 1/1981 | Farina et al. .......................... 422/72 |
| 4,297,104 | 10/1981 | Claude .................................. 422/72 |

FOREIGN PATENT DOCUMENTS

| 814955 | 3/1937 | France ................................ 366/218 |
| 1420663 | 1/1976 | United Kingdom . |

Primary Examiner—Christine M. Nucker
Attorney, Agent, or Firm—Parkhurst & Oliff

[57] ABSTRACT

A method of reacting a first reactive substance bonded to the inner wall surface of a reaction vessel and a second reactive substance in a liquid phase in the vessel by rotating the reaction vessel about its axis at a speed of 10 to 100 rpm, while said reaction vessel is kept inclined at an angle between 5° and 45° to the horizon with its mouth being raised; and an apparatus usable for practicing this method.

29 Claims, 9 Drawing Figures

METHOD FOR REACTING SOLID AND LIQUID PHASES

BACKGROUND OF THE INVENTION

The present invention relates to a method and an apparatus for reacting solid and liquid phases. More specifically, it relates to a method of efficiently reacting a reactive substance bonded on a solid phase and a reactive substance in a liquid phase, and an apparatus used for carrying out the method.

There has been known an immunological method which employs an antigen-antibody reaction for determining the quantity of a very small amount of substance in body fluids, or for determining the concentration of an administered medicine in blood or urine in an organism. Several methods, which are based on different principles of determination, have been known and put in practical use. They include radio-immunoassay (RIA), enzyme-immunoassay (EIA) and fluorescent-immunoassay (FIA), which have been widely employed because of their high sensitivity, and their high effectiveness in quantitative determination. When these assays are carried out, the so-called sandwich method or the competitive method is employed as an assay principle. Particularly sandwich method is widely used, since it provides a high degree of analytical sensitivity and is easy to carry out.

According to the sandwich method, the antigen to be measured is reacted with an insolubilized corresponding antibody (first reaction), whereby an antigen-antibody complex is formed. This complex is reacted with an antibody labeled with a labeling agent and capable of combining with the antigen to be measured (labeled antibody) (second reaction). Then, the labeled antibody is divided into two portions; one has combined to the antigen-antibody complex, and another has not, and the activity of the labeling agent in either portion is measured. On the other hand, similar procedures are repeated for an antigen at known concentrations to establish a calibration curve. The quantity of the antigen to be determined is obtained from the calibration curve. The labeling agent may be, for example, an enzyme, or a radioactive or fluorescent substance.

According to the competitive method, which has been first employed in the radio-immunoassay, the measurement is carried out as follows:

When the antigen to be measured and a given amount of the labelled antigen are reacted with the insolubilized antibody corresponding to the antigen to be measured, both antigens competitively combine with the insolubilized antibody. Next, the labelled antigen is divided into two portions; one has combined to the insolubilized antibody and another has not, and the activity of the labelling agent in either portion is measured. On the other hand, similar procedures are repeated for an antigen at known concentrations to establish a calibration curve. The quantity of the antigen to be determined is obtained from the calibration curve.

In carrying out these reactions, it is advantageous to use the inner wall surface of a vessel as a carrier for a reactive substance such as an antibody to be insolubilized. For example, a plastic test tube is often used, since it serves both as a carrier for insolubilization and as a reaction vessel and it is easy to handle. The inner wall surface of a reaction vessel is, however, disadvantageous in that its surface area to which an antibody or other reactive substance is fixed is smaller than in the case of other carriers, such as plastic beads, filter paper or cellulose particles, and therefore can carry only a smaller quantity of the reactive substance. Consequently, a reaction time therefore becomes longer according to the conventional method in which a test tube or other reaction vessel carrying an insolubilized reactive substance on its inner wall surface is kept upright to stand still, or its contents are stirred intermittently.

SUMMARY OF THE INVENTION

The object of the present invention is to provide a method of efficiently reacting a reactive substance fixed on a solid phase and a reactive substance in a liquid phase.

In particular, the object of the present invention is to provide an improved reaction method for determining the amount of a reactive substance in a liquid phase by a reactive substance fixed on a solid phase.

More specifically, the object of the present invention is to provide a rapid reaction method for measuring an antigen or antibody in a liquid phase by an antibody or antigen or a complex of these fixed on a solid phase.

Another object of the present invention is to provide apparatuses on which reaction vessels are rotated in an inclined position for carrying out the above method.

Other objects and features of the present invention will be more apparent to those skilled in the art on consideration of the accompanying drawings and following specification wherein are disclosed exemplary embodiments of the invention with the understanding that such variations and modifications may be made therein as fall within the scope of the appended claims without departing from the spirit of the invention.

DETAILED DESCRIPTION OF THE INVENTION

Figure 1:
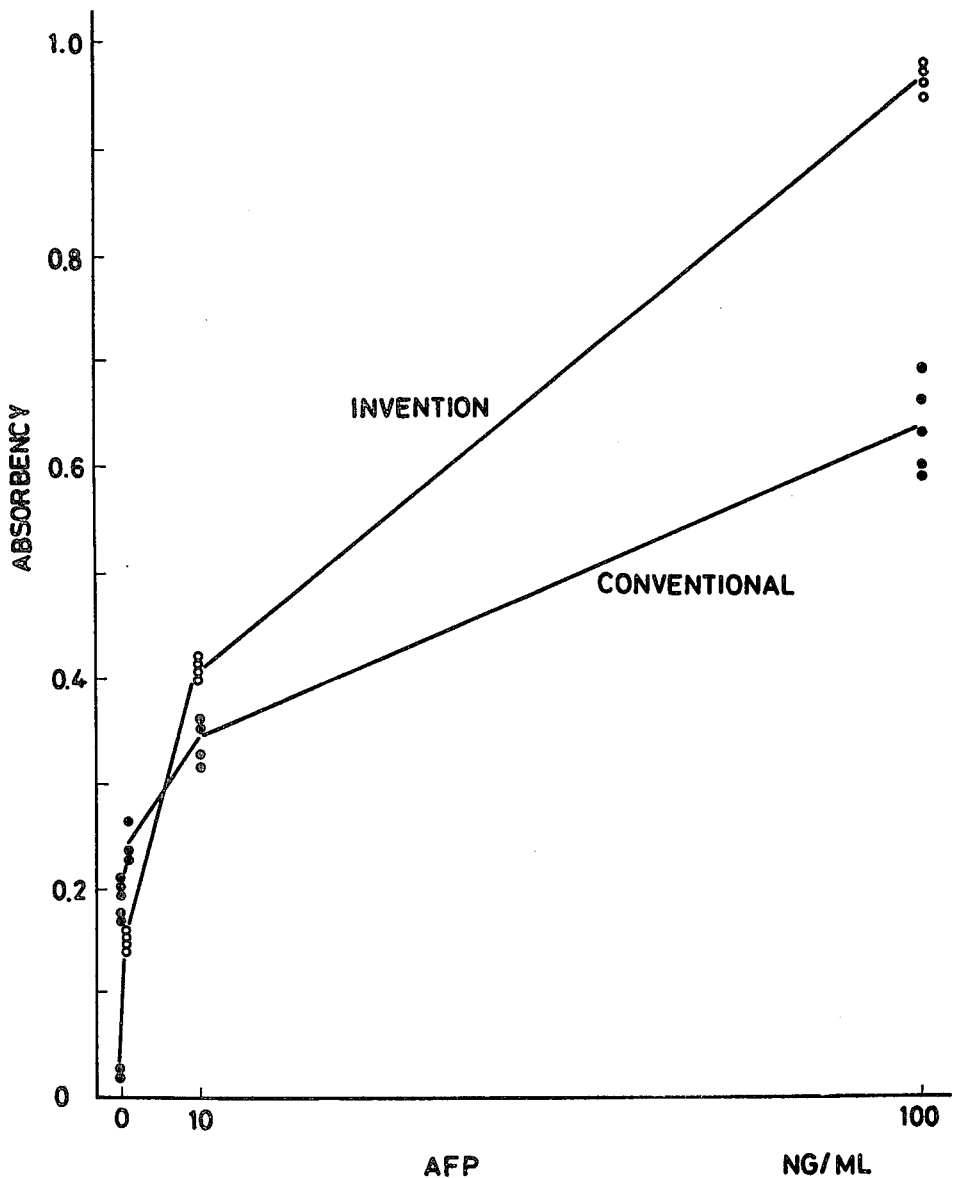
FIG. 1 is a graph comparing the calibration curves obtained in accordance with the method of this invention and the method known in the art.

The present inventors have conducted an extensive study to eliminate the above disadvantages of the conventional method employing a reaction vessel as a carrier for insolubilization. As a result, they have discovered that a higher degree of sensitivity and reduction in time of reaction can be attained when the reaction vessel is inclined at a certain angle and rotated at a certain speed during reaction, instead of being kept upright to stand still or having its contents being stirred intermittently. This discovery has led to this invention.

This invention, thus, provides a method for reaction in which a reaction vessel is rotated in an inclined position, and an apparatus for carrying out the method. In the following description, the reaction vessel is a test tube, the substance carried on the inner wall surface of the reaction vessel is an antibody, and the substance in the liquid phase is an antigen. This combination is, however, employed only for the convenience of description, and does not mean that this invention is limited to such a combination.

Substances in body fluids usually exist in very small quantities, and the body fluids per se are often available only in a small volume. Any method used for measuring those substances is necessarily required to exhibit a high degree of analytical sensitivity for a sample available only in a very small quantity Therefore, it has been usual to fix an antibody to the inner wall surface of a test tube only in the vicinity of its bottom, for example, in an area up to a height of 1 cm from the bottom of the tube.

To the contrary, the present invention enables an antibody to be fixed on a greater area including the upper portion of a test tube, since the sample, even if it is available only in a small volume, can be brought into wide contact with the antibody if the reaction vessel is rotated in an inclined posture as hereinabove described. Moreover, the rotation of the test tube contributes to stirring its contents, and thereby enables measurement with high sensitivity in a short time.

TABLE 1 shows the relationship between the angle of inclination of the reaction vessel, and the relative quantity of the sample required for wetting the antibody carrying portion of the reaction vessel when the fixed area of the antibody in the vessel is constant. TABLE 2 shows the relationship between the angle of inclination of the reaction vessel, and the area of contact between the sample and the inner surface of the vessel in the event the quantity of the sample is constant.

TABLE 1

| Angle of inclination | Relative volume of sample required |
|---|---|
| 90° (upright) | 1 |
| 45° | About ½ |
| 30° | About ⅓ |
| 20° | About 1/5 |
| 10° | About 1/10 |

TABLE 2

| Angle of inclination | Relative size of contact area |
|---|---|
| 90° (upright) | 1 |
| 40° | About 1.5 |
| 30° | About 2 |
| 20° | About 3 |
| 10° | About 4 |

It is generally true that the larger the contact area of two reactants, the more effectively they can be reacted. As is obvious from TABLE 1, the sample volume required for wetting the constant contact area decreases with a reduction in the angle of inclination of the reaction vessel toward a horizontal position. Accordingly, it is desireable to incline the reaction vessel as close as possible to the horizontal position provided that the liquid to be reacted does not flow out. Even when the inclination of the reaction vessel is very close to horizontal, for example as close as 5° above the horizon, there is no fear that the sample may fail to contact the bottom of the vessel, unless sample volume is extremely small.

Although there is no upper limit in particular to the angle of inclination of the reaction vessel, it is preferable to be kept below 45°, more preferably 10°–20°, in order to save the sample volume and raise analytical sensitivity.

It is also preferable to rotate the inclined reaction vessel at a speed of 10 to 100 rpm, more preferably 25–55 rpm. If the rotation speed exceed 100 rmp, the sample fails to flow down along the tube wall but rotates with the vessel, whereby full contact of the sample with the antibody will deteriorate. A rotation speed lower than 10 rpm, on the contrary, causes considerable reduction of the stirring effect to be created by the rotation of the vessel.

The reaction method of this invention has the following advantages:

(i) The continuous rotation of the reaction vessel ensures sufficient stirring of the reaction mixture, improved reaction efficiency, and high sensitivity and improved accuracy of the assay.

(ii) In order to obtain an assay system of high sensitivity, it has hitherto been usual to employ an increased volume of sample. According to this invention, however, it is sufficient to see a sample volume which is equal to only ½ to 1/10 of that which has hitherto been required, as shown in TABLE 1. This has the same effect as if the conventional method has been carried out with a sample volume of twice to ten times as much as that usually employed.

(iii) In the conventional method, when the volume of sample is small, the gradient of the calibration curve becomes lower, reducing the accuracy of measurements obtained by this method. According to this invention, however, the contact area between the sample and the inner surface of the reaction vessel can be increased to 1.5 to 4 times that which has hitherto been obtained, even if the same small volume of sample is employed, as shown in TABLE 2. As the antibody can be bound to the enlarged area, it is possible to obtain an assay system of high sensitivity and accuracy. TABLE 3 shows the results of an assay for alpha-fetoprotein (AFP) performed by using the same reagent and the same sample volume. Tests were repeated five times at each concentration in accordance with the method of this invention and the conventional method. FIG. 1 shows the calibration curves based on the results of TABLE 3. It is noted that the calibration curve according to this invention has a higher gradient than that of the conventional method, and that the method of this invention provides higher accuracy. These assays for AFP were performed in a reaction vessel inclined at an angle of 10°, and rotated at a speed of 30 rpm.

TABLE

| AFP concentration (ng/ml) | 0 | 1 | 10 | 100 |
|---|---|---|---|---|
| Conventional method | | | | |
| Optical ($\bar{x} \pm$ SE) density | $0.193 \pm 0.007$ | $0.240 \pm 0.007$ | $0.346 \pm 0.009$ | $0.639 \pm 0.019$ |

TABLE -continued

| | | | | |
|---|---|---|---|---|
| CV % | 8.5 | 6.2 | 6.0 | 6.7 |
| Method of this invention | | | | |
| Optical ($\bar{x} \pm$ SE) density | 0.025 ± 0.001 | 0.154 ± 0.002 | 0.412 ± 0.105 | 0.970 ± 0.006 |
| CV % | 7.4 | 2.4 | 2.6 | 1.3 |

Figure 2:
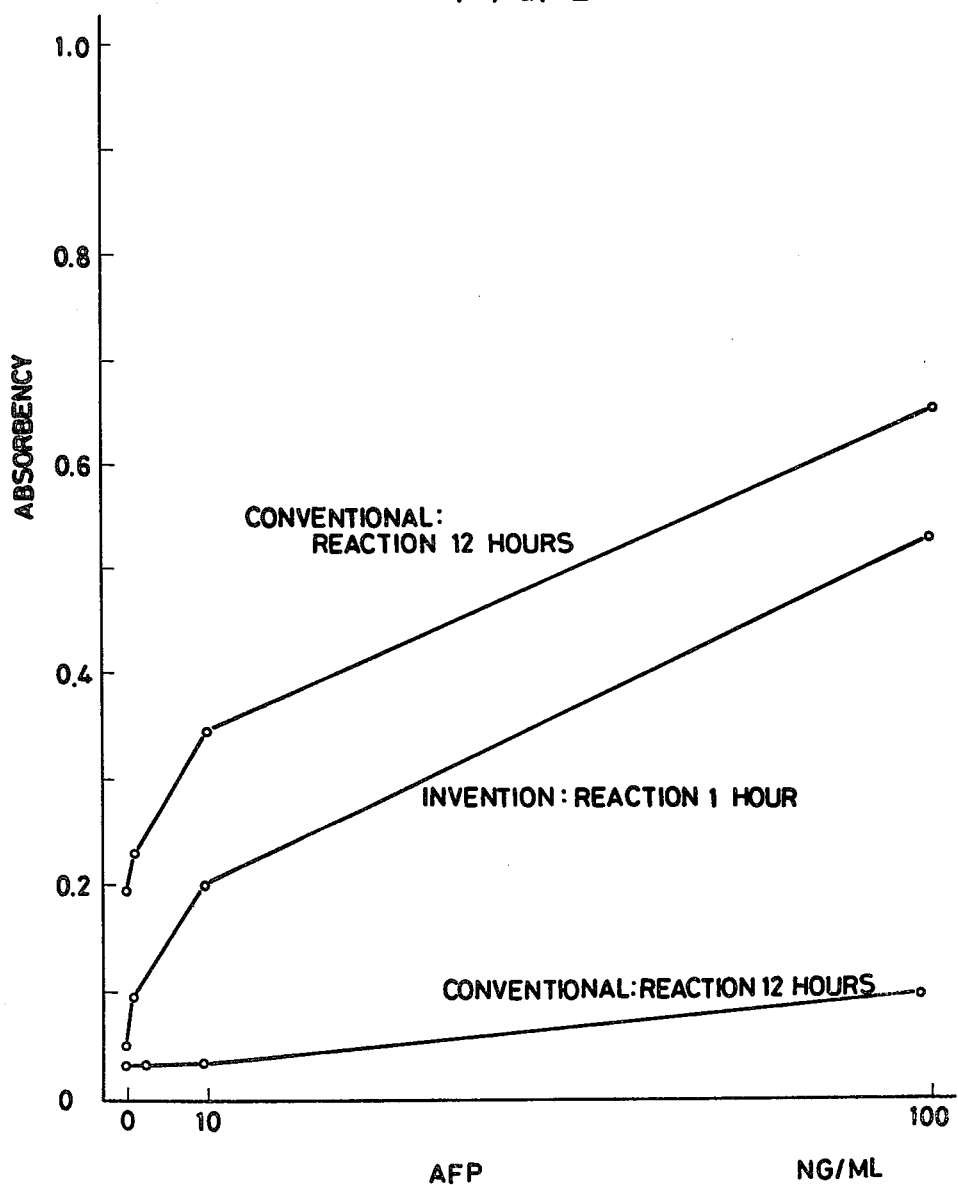
FIG. 2 is a graph showing that the reaction time can be shortened in accordance with the method of this invention.

(iv) The reaction time can be greatly reduced. For example, TABLE 4 shows by comparison assay times required for obtaining similar analytical sensitivities and accuracies, i.e., calibration curves having similar gradients, by using the same reagent in an assay for AFP. The reaction vessel was inclined at an angle of 20°, while it was rotated at a speed of 50 rpm. The standard curves thus obtained are show in FIG. 2. It is noted that the reduction in assay time was so great that the reactions which had required a total of 12 hours according to the conventional method could be accomplished in an hour according to the method of this invention. To the contrary, a shortened reaction time in the conventional standing method resulted in a standard curve having a very small gradient as shown at C in FIG. 2, and consequently failed to perform an assay.

TABLE 4

| | Conventional method (Vessel is kept upright and still) | Method of this invention (Vessel is inclined and rotated) |
|---|---|---|
| First reaction | 60 min. | 20 min. |
| Second reaction | 60 min. | 20 min. |
| Enzyme reaction | 10 hours | 20 min. |

The reaction vessel used in accordance with the method of this invention may, for example, comprise a test tube, optical cell or sample cuvette wherein a reactive substance is fixed on its inner surface to be reacted with a small quantity of sample therein. Preferably, the reaction vessel is a circular or polygonal bottomed cylinder made of glass or plastic having an inside diameter of 5 to 20 mm. The method of this invention may, for example, be applied (i) for reacting an antibody fixed to the inner surface of a reaction vessel with an antigen in a liquid phase, and also in case of EIA by the sandwich method, for example, (ii) for reacting a labeled antibody with the antibody-antigen complex formed by the reaction set forth at (i) above to form a complex comprising the insolubilized antibody-antigen to be assayed—the labeled antibody, or (iii) for reacting an enzyme substrate with the complex set forth at (ii) above to accomplish an enzyme reaction.

In case of the competitive reaction method, the method of this invention may be employed when the antigen to be measured and the labelled antigen are reacted with the insolubilized antibody. Of course, there are many other uses for the method and apparatus of this invention which will occur to those of skill in the art, and this invention is not to be construed as limited to this particular use.

In order to incline and rotate the reaction vessel so as to carry out the method of this invention, it is possible to use any means or apparatus so long as it can hold the vessel at a prescribed angle and rotate it at a prescribed speed. For this purpose, however, it may be advantageous to use the specially designed apparatus of this invention which can carry out the method easily and properly.

The apparatus of this invention for rotating a reaction vessel in an inclined position comprises one or more lateral rows of equally spaced holders projecting from an outer surface of a frame, means for rotating the holders in the same direction at a predetermined speed, and means for positioning the frame in such a manner that the holders may be inclined upwardly at a predetermined angle above the horizon.

Figure 5:
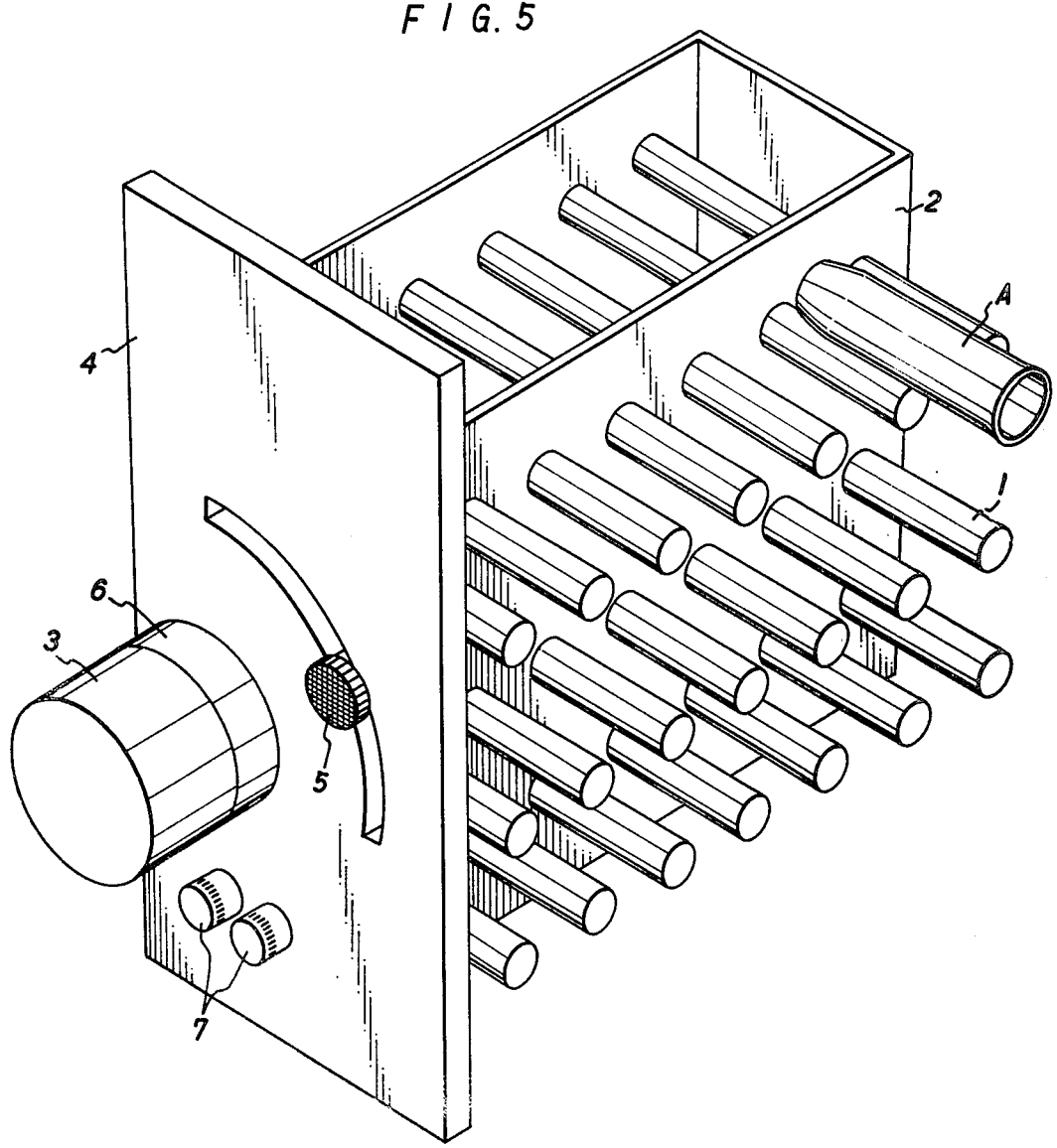
FIG. 5 is a view showing an apparatus embodying this invention.

The apparatus will now be described in further detail with reference to the drawings. FIG. 5 shows an embodiment of the apparatus according to this invention. Equally spaced longitudinal holders 1 project from an outer surface of a frame 2, and support reaction vessels A thereon. The holders 1 are rotated in the same direction by a motor 3 through a power transmission system which will hereinafter be described with reference to FIG. 6. The rotation speed of the holders can be selected in the range of 10 to 100 rpm by a controller 7. The frame 2 is fixed by a screw 5 on a stationary base 4 so that the holders 1 projecting from its outer surface may be inclined upwardly at an angle between 0° and 90° to the horizon. Sheaths of desired diameter may be placed to cover the holders 1 to adjust the distance between two adjoining holders 1 so that the holders 1 may be able to support reaction vessels of desired diameters for rotation thereof.

Figure 6:
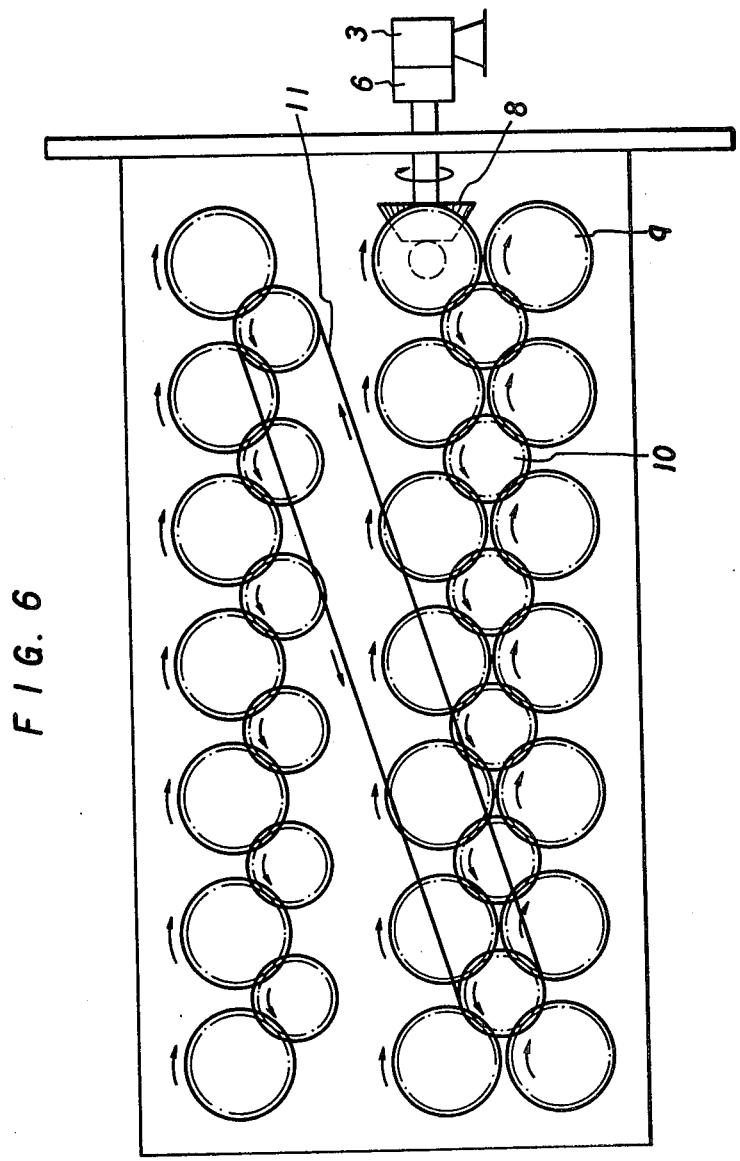
FIG. 6 is a view illustrating a power transmission system for the apparatus of FIG. 5.

FIG. 6 shows the apparatus in FIG. 5 as seen from its back opposite to the holders 1, and illustrates the power transmission system therefor. The rotation of the motor 3 is reduced by a speed reducer 6 to a prescribed level, and transmitted through a bevel gear 8 to one of gears 9 which are coaxial with the holders 1. The rotation of the coaxial gear 9 is transmitted to the adjoining coaxial gears 9 one after another through intermediate gears 10 which regulate the direction of rotation, whereby all the holders 1 are rotated in the same direction. If a large vertical spacing is desired between the adjacent rows of holders 1, it is possible to enlarge the distance between rows of intermediate gears 10 on the rear side of the frame 2, and provide a chain between one of the intermediate gears in one row and one of the intermediate gears in another row.

This invention may also employ another apparatus which comprises a conveyor means such as a conveyor chain having a conveying surface on which freely rotatable rollers are mounted, means for driving the conveyor means in one direction at a speed having a prescribed range, a belt moving to rotate the reaction vessels in a predetermined direction at a predetermined speed while contacting the reaction vessels mounted on the rollers, and means for holding the reaction vessels in an inclined position at a predetermined angle to the horizon with their mouths being raised.

Figure 7:
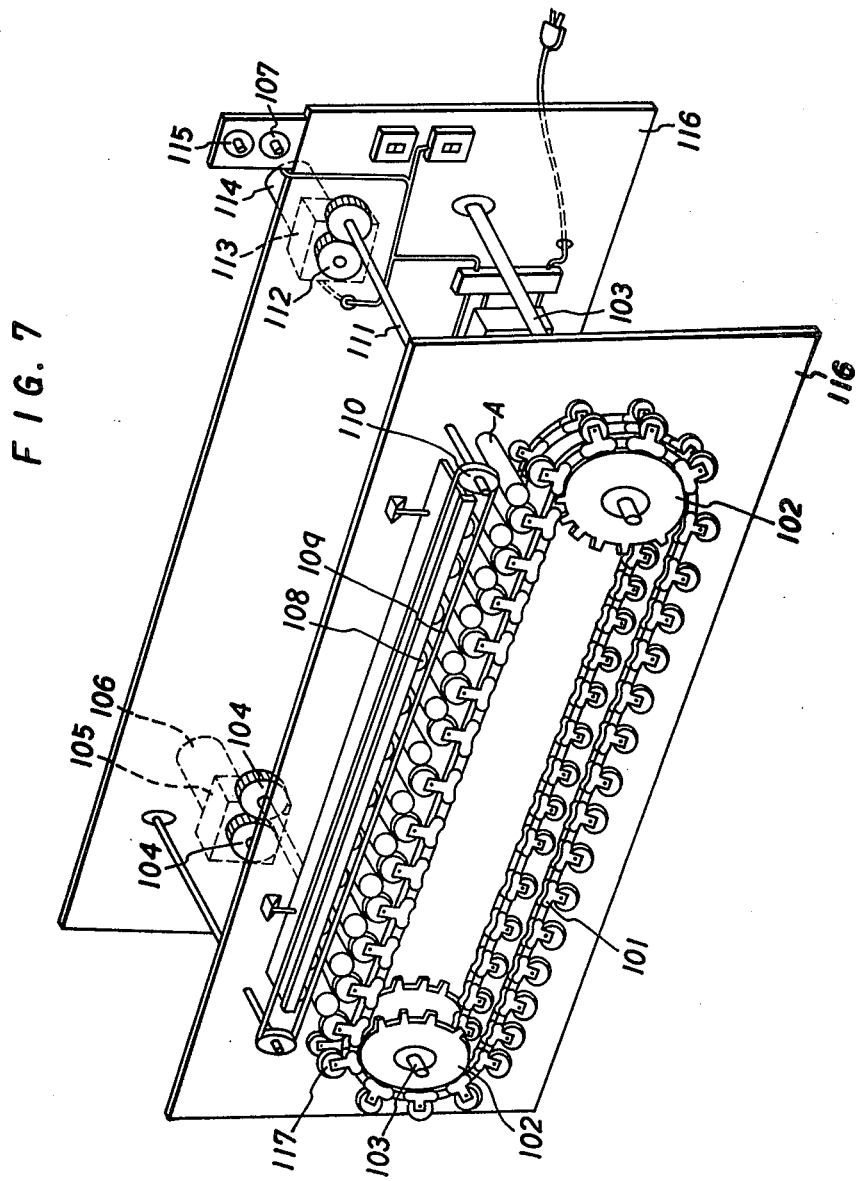
FIG. 7 is a view showing another apparatus embodying this invention.
Figure 8:
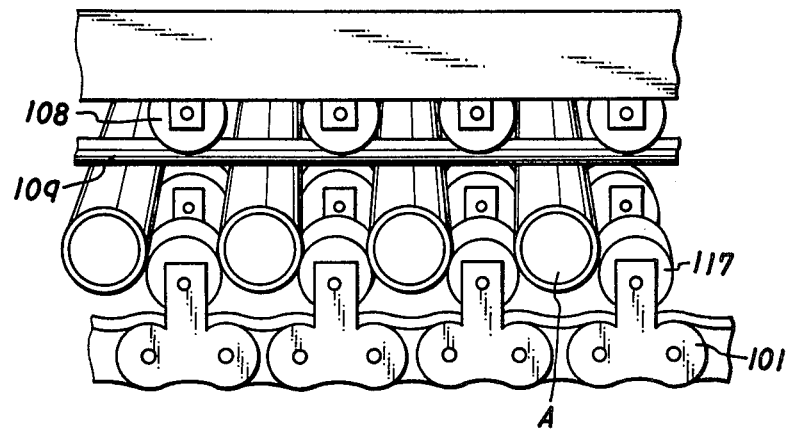
FIGS. 8 and 9 are fragmentary enlarged views showing the mode in which reaction vessels are mounted in the apparatus of FIG. 7.
Figure 9:
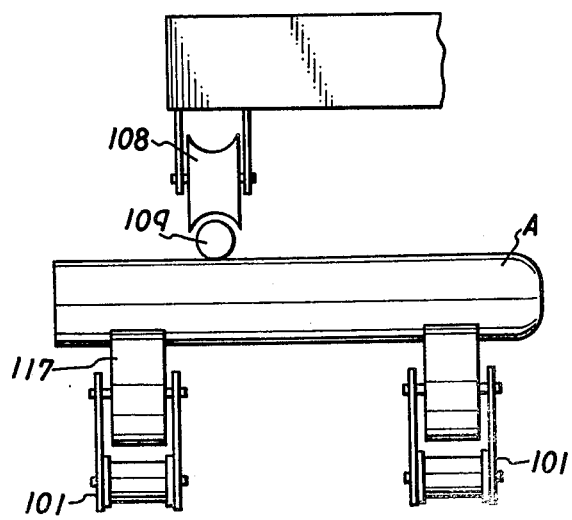

This apparatus will be described in further detail with reference to the drawings. FIG. 7 shows another embodiment of the apparatus according to this invention, and FIGS. 8 and 9 are fragmentary enlarged views showing the mode in which the reaction vessels are supported in the apparatus of FIG. 7. A conveyor chain 101 has a conveying surface in which freely rotatable rollers 117 are mounted. Reaction vessels A are supported on the rollers 117. The chain 101 is driven by a motor 106 through a speed reducer 105, gears 104, shafts 103 and sprockets 102 to move the reaction vessel progressively in one direction. The time for moving the roller in one position to an adjoining roller position can be selected as desired, preferably in the range of 0.5 to 5 minutes, by means of a controller 107.

The reaction vessels are rotated by a belt 109 urged against the vessels by means of press rollers 108. The belt 109 is driven by a motor 114 through a speed reducer 113, gears 112, shafts 111 and pulleys 110. The speed of the belt can be controlled by a controller 115 to rotate the reaction vessels at a speed of 10 to 100 rpm.

The apparatus is, for example, mounted on the support plates 116 so that the reaction vessels may have their axis disposed at an angle between 0° and 90° to the horizontal with their mouths being raised.

The apparatus may be used for transferring the reaction vessels one after another automatically, while they are rotated continuously and their contents are stirred continuously. Accordingly, it is, for example, possible to mount a multiplicity of reaction vessels each containing a sample liquid one after another on the conveyor chain at its starting position, cause the reaction to be completed in the reaction vessel while they are rotated and transferred forward automatically, and examine the results of the reaction in a predetermined position automatically by, for example, a spectrophotometer. Thus, the apparatus of this invention is particularly suitable for automation of the assay system. It is apparent that changes may be made to the exemplary apparatus described herein without departing from the scope of the invention as claimed below.

The reaction method of this invention will now be described with reference to examples.

EXAMPLE 1

ASSAY FOR AFP (a) Preparation of Reaction Test Tubes 2 ml of monoclonal anti-AFP antibody [A] (1 mg/ml) was placed in each polystyrene test tube (12 mm in diameter and 100 mm in height) and the incubation was performed at 50° C. for 20 minutes. Then, each test tube was washed with 0.05M phosphate buffered saline solution (PBS) of pH 6.4 to give a test tube sensitized with the antibody [A]. Another monoclonal antibody [B] of a clone different from that of [A] was labeled with horseradish peroxidase (Boehringer Manheim Grade I, which will hereinafter be referred to simple as HRPO) by the method of Nakane et al. described in J. Histochem. Cytochem., 22, 1084 (1974). The antibody was diluted with PBS 49 to 1, and 1 ml of the diluted antibody was placed in each polystyrene test tube sensitized with the antibody [A]. After the test tubes had been lyophilized they were tightly closed to provide test tubes for AFP assay.

(b) Assay for AFP

Test tubes for AFP assay prepared as described at (a) above were charged with 0.9 ml of PBS. Each test tube was placed in 0.1 ml of standard AFP solution prepared by diluting AFP with normal human serum to contain 1, 10, 100 or 1,000 ng of AFP per milliliter. The test tubes were mounted on the holders in the apparatus of FIG. 5 while inclined upwardly at an angle of 20° to the horizon. The reaction was carried out for 30 minutes, while the test tubes were rotated at a speed of 50 rpm. After the reaction, the test tubes were washed with physiological saline solution containing 0.005% of Tween 20 (hereinafter referred to as washing agent). Each test tube was, then, charged with 2 ml of an enzyme substrate solution containing 50 mg/dl of 5-amino-salicylic acid and 0.01% of hydrogen peroxide. The test tubes were again mounted on the holders while inclined upwardly at an angle of 20° to the horizon, and the reaction was carried out for 30 minutes, while the test tubes were rotated at a speed of 50 rpm.

Figure 3:
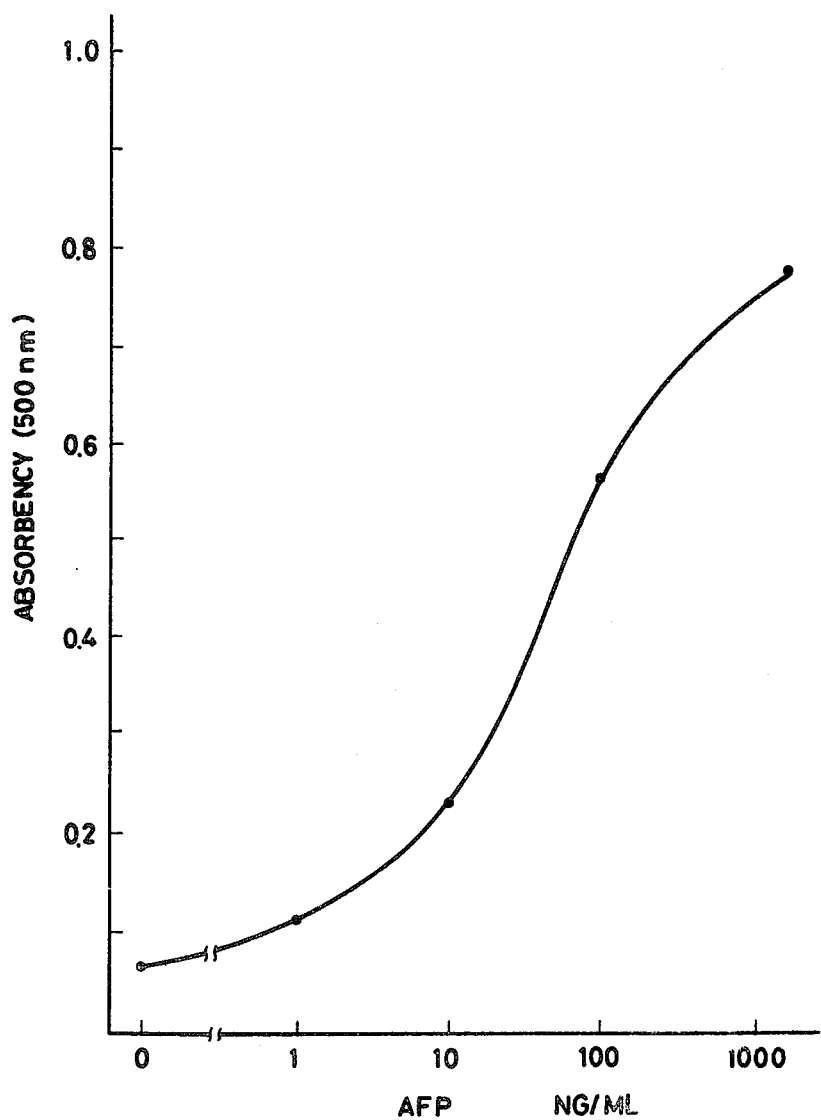
FIG. 3 is a graph showing a standard curve for the AFP assay in EXAMPLE 1.

Then, 50 μl of 2% sodium azide was added to terminate the reaction. The absorbency of the reaction mixture was examined at a wavelength of 500 nm by a spectrophotometer. The calibration curve obtained therefrom is shown in FIG. 3.

EXAMPLE 2

ASSAY FOR CEA (a) Preparation of Reaction Test Tubes

Each polystyrene test tube (8 m in diameter; 100 mm in height) was charged with 2 ml of monoclonal anticarcinoembryonic antigen (CEA) antibody [A'] (1 mg/ml), anc it was incubated at 56° C. for 20 minutes. Then, the test tube was washed with PBS to give a test tube sensitized with the CEA antibody [A'].

Another monoclonal antibody [B'] of a different clone from that of [A'] was labeled with HRPO in accordance with the method described at (a) in EXAMPLE 1. The antibody was diluted with PBS to 50 volumes, and 1 ml of the diluted antibody was placed in each test tube sensitized with the CEA antibody [A']. After the test tubes had been lyophilized, they were tightly closed to provide test tubes for CEA assay.

(B) Assay for CEA

Figure 4:
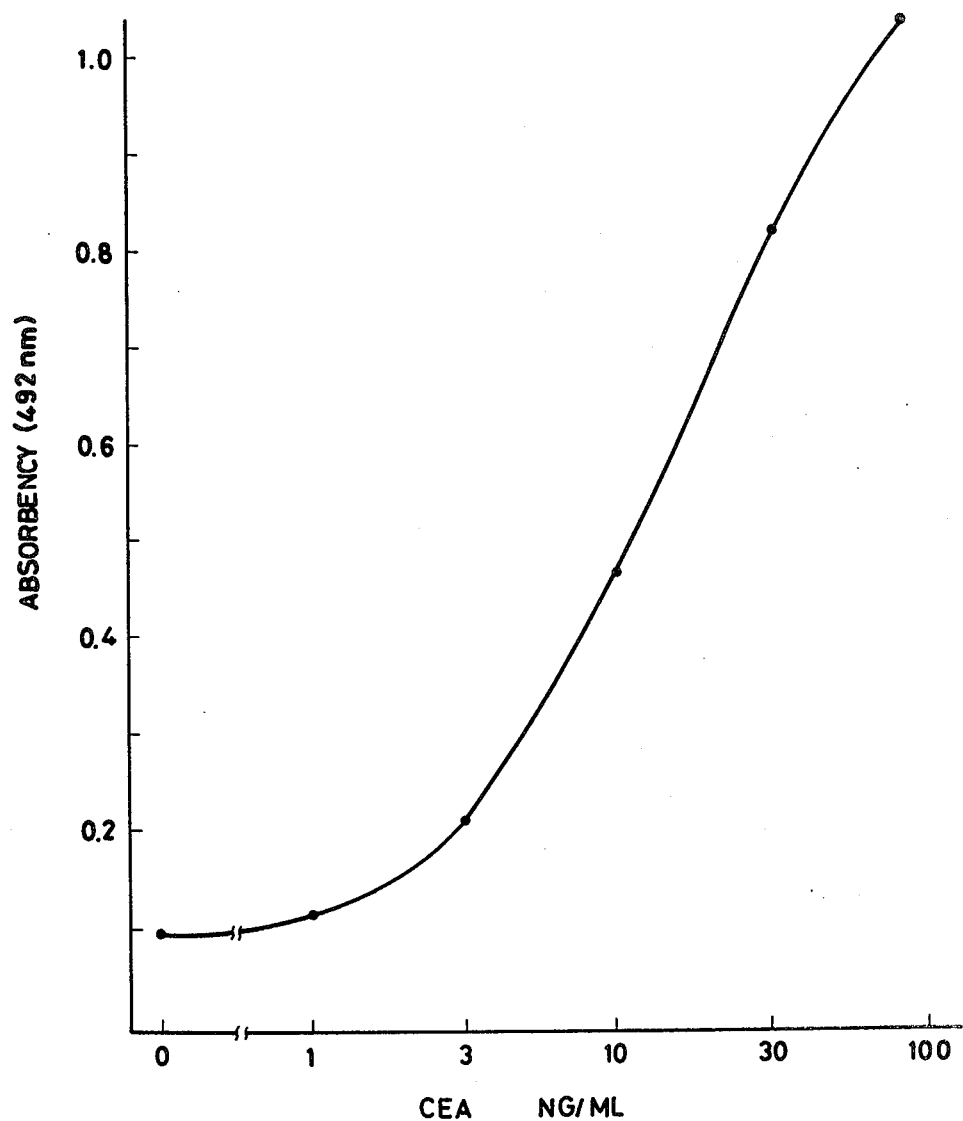
FIG. 4 is a graph showing a standard curve for the CEA assay in EXAMPLE 2.

Test tubes prepared as described at (a) above were each charged with 0.9 ml of PBS, and 0.1 ml of standard CEA solution prepared by diluting CEA with normal human serum to contain 1, 3, 10, 30 or 100 ng of CEA per milliliter. The test tubes were mounted on the conveyor chain in the apparatus of FIG. 7 while inclined upwardly at an angle of 10° to the horizon. The reaction was carried out for 20 minutes while the test tubes were rotated at a speed of 30 rpm. Then, each test tube was washed with the washing agent, and charged with 2 ml of an enzyme substrate solution containing 100 mg/dl of o-phenylenediamine and a 0.3% aqueous solution of hydrogen peroxide. The test tubes were again mounted on the conveyor chain while inclined upwardly at an angle of 10° to the horizon. The reaction was carried out for 20 minutes, while the test tubes were rotated at a speed of 30 rpm. Them, 0.5 ml of 4N hydrochloric acid was added to terminate the reaction. The absorbency of the reaction product was examined at a wavelength of 492 nm by a spectrophotometer. The calibration curve obtained therefrom is shown in FIG. 4.

We claim:

1. A method of reacting a first reactive substance bound to the inner wall surface of a reaction vessel and a second reactive substance in a liquid phase, said method comprising placing a liquid containing said second reactive substance in said reaction vessel and rotating said reaction vessel about its axis at a speed of 10 to 100 rpm, while said reaction vessel is kept inclined at an angle between 5° and 45° above the horizontal.

2. A method as set forth in claim 1, wherein the reaction vessel is kept inclined at an angle between 10° and 20° above the horizontal.

3. A method as set forth in claim 1 or 2, wherein the speed of rotation is from 25 to 55 rpm.

4. A method as set forth in claim 1 or 2, wherein said first reactive substance is an antigen or antibody, while said second reactive substance is a corresponding antibody or antigen.

5. A method as set forth in claim 1 or 2, wherein said first reactive substance is an antibody, while said second reactive substance is a mixture of a corresponding antigen and a labeled antigen obtained by labeling said antigen with a labeling agent selected from the group consisting of radioactive isotopes, enzymes and fluorescent substances.

6. A method as set forth in claim 1 or 2, wherein said first reactive substance is a complex of an insolubilized antibody and a corresponding antigen, while said second reactive substance is a labeled antibody corresponding to said insolubilized reactive substance and labeled with a labeling agent selected from the group consisting of radioactive isotopes, enzymes and fluorescent substances.

7. A method as set forth in claim 1 or 2, wherein said first reactive substance is a complex of an insolubilized antibody and a corresponding labeled antigen, while said second reactive substance is an enzyme substrate.

8. A method as set forth in claim 1 or 2, wherein said first reactive substance is a complex of an insolubilized antibody, a corresponding antigen and an antibody labeled with an enzyme, while said second reactive substance is an enzyme substrate.

9. A method as set forth in claim 1 or 2, wherein said reaction vessel is a circular bottomed cylinder made of a material selected from the group consisting of glass and plastic, and has an inside diameter of 5 to 20 mm.

10. A method as set forth in claim 1 or 2, wherein said first reaction vessel is a polygonal bottomed cylinder made of a material selected from the group consisting of glass and plastic, and has an inside diameter of 5 to 20 mm.

11. A method as set forth in claim 3, wherein said first reactive substance is an antigen or antibody, while said second reactive substance is a corresponding antibody or antigen.

12. A method as set forth in claim 3, wherein said first reactive substance is an antibody, while said second reactive substance is a mixture of a corresponding antigen and a labeled antigen obtained by labeling said antigen with a labeling agent selected from the group consisting of radioactive isotopes, enzymes and fluorescent substances.

13. A method as set forth in claim 3, wherein said first reactive substance is a complex of an insolubilized antibody and a corresponding antigen, while said second reactive substance is a labeled antibody corresponding to said insolubilized reactive substance and labeled with a labeling agent selected from the group consisting of radioactive isotopes, enzymes and fluorescent substances.

14. A method as set forth in claim 3, wherein said first reactive substance is a complex of an insolubilized antibody and a corresponding labeled antigen, while said second reactive substance is an enzyme substrate.

15. A method as set forth in claim 3, wherein said first reactive substance is a complex of an insolubilized antibody, a corresponding antigen and an antibody labeled with an enzyme, while said second reactive substance is an enzyme substrate.

16. A method as set forth in claim 3, wherein said reaction vessel is a circular bottomed cylinder made of a material selected from the group consisting of glass and plastic, and has an inside diameter of 5 to 20 mm.

17. A method as set forth in claim 3, wherein said reaction vessel is a polygonal bottomed cylinder made of a material selected from the group consisting of glass and plastic, and has an inside diameter of 5 to 20 mm.

18. An apparatus for rotating one or more reaction vessels in an inclined position, comprising one or more lateral rows of equally spaced holders projecting from an outer surface of a frame, means for rotating said holders in the same direction at a predetermined speed, and means for positioning said frame in such a manner that said holders may be inclined upwardly at a predetermined angle to the horizontal.

19. An apparatus as set forth in claim 18, wherein said predetermined speed is within a range of 10 to 100 rpm and said predetermined angle is from 5° to 45°.

20. An apparatus as set forth in claim 19, wherein the predetermined speed is from 25 to 55 rpm.

21. An apparatus as set forth in claim 19 or 20, wherein the predetermined angle is from 10° to 20°.

22. An apparatus for rotating at least one reaction vessel in an inclined position, comprising a conveyor means having a conveying surface on which freely rotatable rollers are mounted, means for driving said conveyor means in one direction at a speed having a prescribed range, a belt contacting said reaction vessel mounted on said rollers and moving to rotate said reaction vessel in a predetermined direction at a predetermined speed, and means for holding said reaction vessel in an upwardly inclined position at a predetermined angle to the horizontal.

23. An apparatus as set forth in claim 22, wherein said predetermined speed is from 10 to 100 rpm and said predetermined angle is from 5° to 45°.

24. An apparatus as set forth in claim 23, wherein the predetermined speed is from 25 to 55 rpm.

25. An apparatus as set forth in claim 23 or 24, wherein the predetermined angle is from 10° to 20°.

26. An apparatus as set forth in claim 22, wherein said conveyor means is a conveyor chain.

27. An apparatus as set forth in claim 23, wherein said conveyor means is a conveyor chain.

28. An apparatus as set forth in claim 24, wherein said conveyor means is a conveyor chain.

29. An apparatus as set forth in claim 25, wherein said conveyor means is a conveyor chain.

* * * * *

UNITED STATES PATENT AND TRADEMARK OFFICE
CERTIFICATE OF CORRECTION

PATENT NO. : 4,482,636

DATED : November 13, 1984

INVENTOR(S) : Ei MOCHIDA et al

It is certified that error appears in the above-identified patent and that said Letters Patent is hereby corrected as shown below:

Please delete claims 18-29.

Title page:

"29 Claims" should read --17 Claims--.

Signed and Sealed this

Nineteenth Day of April, 1988

Attest:

DONALD J. QUIGG

*Attesting Officer*   *Commissioner of Patents and Trademarks*